United States Patent [19]

Gereg

[11] 4,351,331
[45] Sep. 28, 1982

[54] ENDOTRACHEAL TUBE HOLDER AND BITE BLOCK

[76] Inventor: Gordon A. Gereg, 557-A Blue Church Rd., Coopersburg, Pa. 18036

[21] Appl. No.: 202,696

[22] Filed: Oct. 31, 1980

[51] Int. Cl.³ .............................................. A61M 25/02
[52] U.S. Cl. ....................... 128/207.17; 128/DIG. 26
[58] Field of Search ..................... 128/207.14, 207.15, 128/207.16, 207.17, 200.26, DIG. 26

[56] References Cited

U.S. PATENT DOCUMENTS

| | | | |
|---|---|---|---|
| 2,908,269 | 10/1959 | Cheng | 128/207.14 |
| 3,782,388 | 1/1974 | Page | 128/DIG. 26 |
| 4,068,658 | 1/1978 | Berman | 128/200.26 |
| 4,235,229 | 11/1980 | Ranford et al. | 128/207.17 |
| 4,249,529 | 2/1981 | Nestor et al. | 128/207.17 |

Primary Examiner—Henry J. Recla

[57] ABSTRACT

An endotracheal tube holder made in one simple piece that slips over the tube from one side and locks in place by a snap action. The use of plastic material provides a hinge for opening and closing the holder with the resiliency of the plastic providing a snap action for locking and unlocking the device. The lock is a positive one resulting from the abutting of two flat members and guards against further closure as well as opening. The portion in the patient's mouth is reinforced to provide a bite block. A flange against the lips and face allow fastening to the patient with tape, straps or adhesive means. Openings are provided to allow access for probes or catheters alongside the endotracheal tube.

9 Claims, 4 Drawing Figures

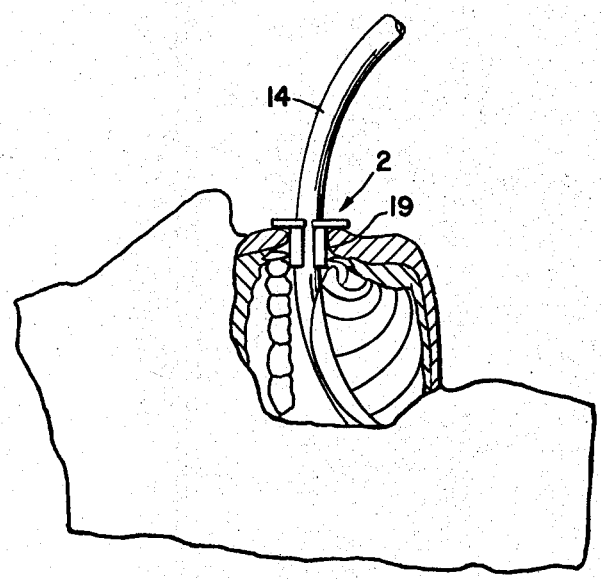
Fig 3
Fig 4
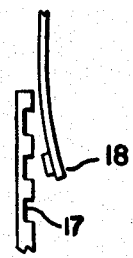

ENDOTRACHEAL TUBE HOLDER AND BITE BLOCK

FIELD OF INVENTION

Surgery, Cannula, Holder, Tracheal

OBJECTS

Endotracheal tubes placed in the trachea through the mouth to convey gases to the lungs can be held in place by friction in the trachea. Newer tube designs used low pressure in the sealing cuffs to lessen contact pressure on the trachea which reduces the holding action necessitating fixing the tube by other means. Many users commonly tape the tube to the patient's face which is inconvient and somewhat difficult because the tube axis is at right angles to the face.

There have been attempts to provide flange like holders which are fixed to the tube with tape or similar means. Using tape means the holder cannot be readily repositioned on the tube. Also most of the previous holders had to be installed over the end of the tube meaning it had to be installed before the connections to the tube were made. After installation is a much better time for the anesthesiologist. Also repositioning a taped on holder is difficult.

A bite block is needed to prevent a patient from occluding the tube during a seizure. Some previous holders included bite blocks but they did not have a wide flat surface to avoid damage to the teeth and were often inadequate for patients with missing teeth.

This invention solves the problems of previous holders by providing a simple to use, inexpensive device that snaplocks in place and while firmly fixing the tube provides a bite block as well. The device is adaptive to various methods of fixing it to the patient including straps or adhesive means. Removing or repositioning the holder after use is far simpler than any other previous design as it can be snapped to spring open.

These and other objects will be apparent from the following specifications and drawings, in which:

FIG. 3 is a plan view of the device in a sectional view of a patient showing the positioning of the device.

FIG. 4 is a partial plan view of a lock variation.

Figure 1:
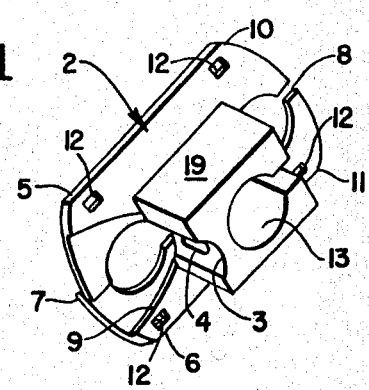
FIG. 1 is a perspective view of the device in the open mode.

Referring now to the drawings, in which like reference numerals denote similar elements, the holder assembly is denoted generally by the numeral 2 and is shown in FIG. 1 in the open position. The device must be held in the open position as when placing it on a tube by a force applied at the top and bottom denoted by numerals 5 and 6 of the side opposite the opening by squeezing between the thumb and index finger while the top and bottom of area 7 overlap one another. The natural spring action of the plastic material will cause the holder to be closed but not locked when relaxed and without an endotracheal tube in place. The material from which the part would be molded would be a semi-rigid material such as, but not limited to, polypropylene, polyallomer or acetal plastic. These materials can be made with a thinned down section which are known to persons skilled in the art as living hinges which have the ability to withstand many flexures. The thickness changes in area 3 and also the material left after holes 4 and 15 are molded in is in line with the proper design of living hinges.

The open side 8 also is molded with a thin opening similar to lock side 7. When the holder is closed by a force on areas 10 and 11 by squeezing with the thumb and index finger the top and bottom halves will meet at 8 and a positive stop will be made. At the time the stop is reached, the lock 7 will be in a position to snap into place in a flat plane having been overlapped while the holder was open. With an endotracheal tube of the proper size in place as in FIG. 2 there would be some force trying to open the holder due to having the hole 13 in the holder smaller than the tube 14 by a small amount. This interference would provide the tight grip needed to hold the tube and also allow the holder to easily spring open when the lock was twisted to release the tension on it.

It is desirable and easy to mold certain features into the holder to enhance its performance. The holder would be molded in the closed mode but complete with all slots and openings so no secondary operations would be necessary. The part could be easily molded with a single opening mold with all corepins withdrawing from one side. When the part was removed from the mold and still warm, the area 7 used to lock the holder would be twisted so the upper and lower portions which would be molded in one flat plane could be made to pass by each other to allow the opposite side 8 to open. By doing this operation at the molding site, a slight orientation could be given to the lock area and any flashing of the thin opening could be detected for correction. It is expected that when the part was closed the lock area would snap back to a very nearly flat plane.

The lock area 7 is thinner than the surrounding area 5 and 6 to provide a flexible area for the springing of the lock and also the shape is chosen so when the device is in the full open position, the edges of the lock 7 will be stopped against a step 9. In this way it will not be possible to over stress the plastic and possibly break the hinge. Making area 5 and 6 thicker makes the contact with fingers more comfortable. A rather wide ledge for better gripping could easily be provided across the entire top and bottom in the areas between 5 and 10 and 6 and 11.

Figure 2:
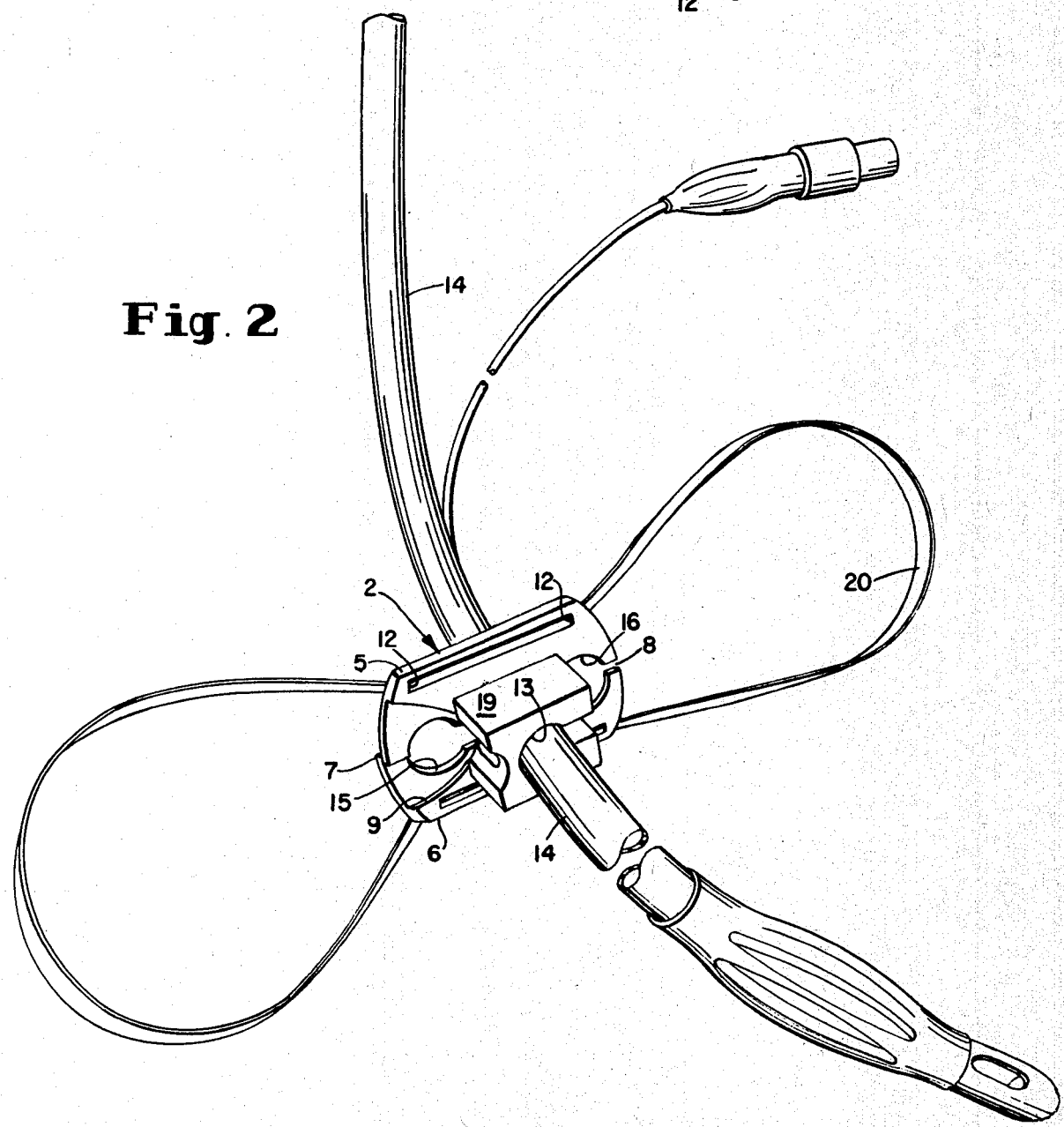
FIG. 2 is a perspective view of the device locked on an endotracheal tube.

The flange area with lock 7 and stop 8 is shown generally flat but need not be limited to this shape if it is desired to make it conform more closely to a patients face. In FIG. 2 a band 20 which may or may not be elastic is shown attached to the flange by slots 12. Protrusions or lugs could also be provided for the same purpose. The band could pass around the ears or around the entire head to fit the holder in place. Simply taping the holder to the face would be an easy and workable way to fix the holder. It would also be possible to provide adhesive strips on the holder either on the back (perhaps in conjunction with a foam pad) or front.

The flange is shown with holes 15 and 16 which are meant to allow passing other probes or catheters into the patient while the holder is in place. It may be desirable to make them considerably larger than shown to save plastic and also to allow a clearer view of the lips and mouth area. The design is shown with two holes 15 and 16 but need not be limited to two.

The design would be easiest to accomplish if made for only one size tube. If this is not economical or desirable the design could be made to adapt to more sizes by changing the lock area to provide several stops rather than one. This still would be easily molded and would work in a nearly identical way to the single size design. Hole 13 for the tube would be shaped either oval or square (as one triangle up and one triangle down) to provide a grip area for a range of tube sizes. FIG. 4 is a partial plan view of lock area 7 showing a proposed lock variation. The pieces that overlap would now have respectively a series of groves 17 and a lug 18 which would fit into the grooves. The smallest tube would be locked in by an action exactly as described above. Successive larger tubes would cause the holder to be held open slightly and the holder would be stopped by the lug 18 fitting into a particular one of the grooves 17. Lug 18 fitted into grove 17 would set the clamping force and provide a stop when used with tubes other than the smallest intended size. The stop is necessary to prevent occluding the tube if a patient bites down. Release of the lock would be accomplished in the same way as for a single sized holder although it may be necessary to use two hands instead of one to fully open the holder because the lock will want to stop the opening action.

The bite block area 19 is solidly constructed and presents a flat surface to the teeth or gum structure. Being thick and strong provides the support needed to avoid occluding the tube if a patient has a violent seizure and clamps the mouth shut. To protect the patient's teeth or gums if teeth are missing, the surface is smooth and flat. Smaller bite blocks can wedge between teeth or put more pressure on a small area with the possibility of damage. It is also possible to make the molded block slightly smaller and add an insert or covering of soft material to further reduce the possibility of damage to the patient.

In normal operation the user would be presented the holder in a package with the holder slightly open or unlocked. The user would grip the holder between the thumb and index finger at 5 and 6 and squeeze it until it opens far enough to slip over the tube 14 to be held which had been previously put in place in the patient and could be connected to a gas source. The holder 2 would be left unlocked but relaxed over the tube 14 and slid along the tube axis and into the mouth of the patient. When the user was satisfied with its position, it would be locked in place by squeezing down with the thumb and forefinger on areas 10 and 11 until the lock 7 snapped into one place assuming the single size holder was being used. Tape, straps, bands or other suitable attachment means would be applied after the holder was locked in position.

To remove or reposition the holder, the attachments would be removed or loosened. With the thumb and index finger the lock 7 would be twisted slightly to allow the upper and lower areas to pass over or overlap. The tension of clamping down on a slightly oversize tube 14 in relation to hole 13 will cause the holder to spring open slightly as soon as the lock is twisted. By gripping with the thumb and index finger in areas 5 and 6 the holder can be further opened to completely remove it from the tube 14 or to reposition it. There is no difference when used by a right or left handed person or if the holder is put on from the right or left side of the tube.

I claim:

1. A tube holder for use with an endotracheal tube adapted to be inserted through the mouth of a patient, said holder being made as a one-piece structure of resilient material and capable of being moved from a locked position to an unlocked position, said holder comprising a tubular member having an outwardly projecting flange at one end thereof, said tubular member and flange having a bore extending therethrough for receiving said tube, said tube member being split axially along its entire length on one side, said flange having a first split extending from said bore to its peripheral edge and being continuous with said split in said tubular member, said flange also having a second split opposite said first split extending from said tubular member side opposite said one side defining a pivot for said tubular member to its peripheral edge, said first and second split defining alignable abutting surfaces, said tubular member and flange, and connection means for fixing said tube holder on a a patient, whereby said tube holder is unlocked by twisting said flange on either side of said second split and moving said abutting surfaces out of alignment and rotating said flange and tubular member about said pivot thereby causing said abutting surfaces defined by said first split to separate to permit insertion or removal of said tube into or from said bore and said holder is locked by pivoting said tubular member and flange in the opposite direction thereby causing said abutting surfaces defined by said second split to align.

2. A tube holding device as in claim 1 only the lock area of the flange is a series of ratchet like steps to allow use of a single holder on more than one size tube with locking and unlocking with accomplished by the twisting to release the lock and relaxing the flange to let it seat into a step thereby fixing movement that would either open the holder or close it further.

3. A holder for an endotracheal tube as in claim 1 opening on one side which may be installed with one hand after the endotracheal tube is in place and fully connected and which may be repositioned at any time.

4. A bite block or stop for a patient's teeth provided by a heavy section of an endotracheal tube holder as in claim 1 said bite block may or may not be an insert of a softer material. The lock action of the holder providing a positive stop so the holder is not tightened on the tube when bit down on.

5. A holding device for an endotracheal tube as in claim 1 having a flange suitably shaped to suit patient's anatomy and providing an area for attaching means to fix the holder and tube assembly to the patient by straps, bands or adhesive means.

6. A holder for an endotracheal tube as in claim 1 having in addition to the main passage for the endotracheal tube, additional holes in the flange which is wider than the section holding the tube and providing a bite block, through which probes or cannula can be inserted or through which the user can observe the mouth area of the patient.

7. A holding device as in claim 1 using the spring and hinge characteristics of certain plastics to provide an easy to use clamp which provides a means for fixing the position of an endotracheal tube in a patient by clamping the tube with considerable clamp force provided by leverage enhancing the force of the user by providing an extended flange at a distance from the pivot or hinge and a positive lock provided by two edge surfaces butting together on the flange side opposite the pivot and requiring a side force to unlock so the high clamp force can be retained.

8. A locking holder or flange for an endotracheal tube as in claim 1 which has a snap lock utilizing two normally abutting surfaces of a split flange that automatically grips the tube when closed and releases by allowing the abutting surfaces to pass one another after being twisted.

9. A tube holder as in claim 1 being one piece plastic mold with all holes and passages parallel and opening to the same side to allow molding with one parting line and having all core pins withdraw from the same side.

* * * * *